United States Patent [19]

Muller et al.

[11] Patent Number: 4,674,319
[45] Date of Patent: Jun. 23, 1987

[54] INTEGRATED CIRCUIT SENSOR

[75] Inventors: Richard S. Muller, Kensington, Calif.; Roger T. Howe, Pittsburgh, Pa.

[73] Assignee: The Regents of the University of California, Berkeley, Calif.

[21] Appl. No.: 714,076

[22] Filed: Mar. 20, 1985

[51] Int. Cl.⁴ .................. G01N 27/00; H01L 29/84
[52] U.S. Cl. ................................... 73/23; 357/26
[58] Field of Search .............. 73/23; 357/25, 26, 69

[56] References Cited

U.S. PATENT DOCUMENTS

| | | | |
|---|---|---|---|
| 4,471,647 | 9/1984 | Jerman et al. | 73/23.1 |
| 4,549,427 | 10/1985 | Kolesar | 73/23 |
| 4,571,661 | 2/1986 | Hoshino | 357/26 |

OTHER PUBLICATIONS

Howe & Muller, "Polycrystalline Silicon Micromechanical Beams", *J. of Electrochemical Society*, V130, #6, pp. 1420-1423, 6/83.
Howe & Muller, "Polycrystalline Silicon Micromechanical Beams", *Electrochemical Society Mtg*, Montreal, Canada, 5/82 (abstract 118).
Howe & Muller, "Polycrystalline and Amorphous Silicon Micromechanical Beams: *Annealing & Mechanical Prop.*,", (accepted by) Sensors & Actuators, 5/83.

Petersen, "Silicon as a Mechanical Material", *Proceedings of the IEEE*, vol. 70, #5, pp. 420-457, May 1982.

*Primary Examiner*—Stephen A. Kreitman
*Attorney, Agent, or Firm*—Fitch, Even, Tabin & Flannery

[57] ABSTRACT

A polysilicon microstructure is formed on a silicon substrate. Beneath the microstructure, are diffused regions in the substrate. The microstructure is capacitively coupled to these diffused regions so that one such capacitor acts as an excitation capacitor and the other capacitor acts as a sense capacitor. By applying an AC voltage to the excitation capacitor, the electrostatic force between the substrate and the microstructure changes causing a mechanical vibration in the microstructure. A DC voltage is applied to the sense capacitor. The mechanical vibration, which changes its capacitance, will develop a current through the sense capacitor. A phenomenon may then be sensed by the vibrating microstructure. A polymer film disposed on the microstructure can sorb a gas of interest. As the mass of the polymer film and vibrating microstructure increases, its frequency or phase changes. The current through the sense capacitor will exhibit a commensurate frequency or phase shift. Detection of such frequency or phase shift in the sense capacitor current will transduce the detection of the vapor of interest.

16 Claims, 11 Drawing Figures

| BRIDGE | L(μm) | W(μm) | l(μm) | W'(μm) | HOLES | (kHz) | Q |
|---|---|---|---|---|---|---|---|
| 8A | 122 | 9 | 14 | 39 | NO | 433.5 | 21 |
| | 153 | 15 | | | YES | 449 | 22 |
| 8B | | | 18 | 47 | NO | 243 | 7 |
| | | 23 | | | YES | 254 | 12 |
| 8C | 180 | | 22 | 55 | NO | 155 | 2 |
| | | | | | YES | 127.5 | 6 |

FIGURE 7
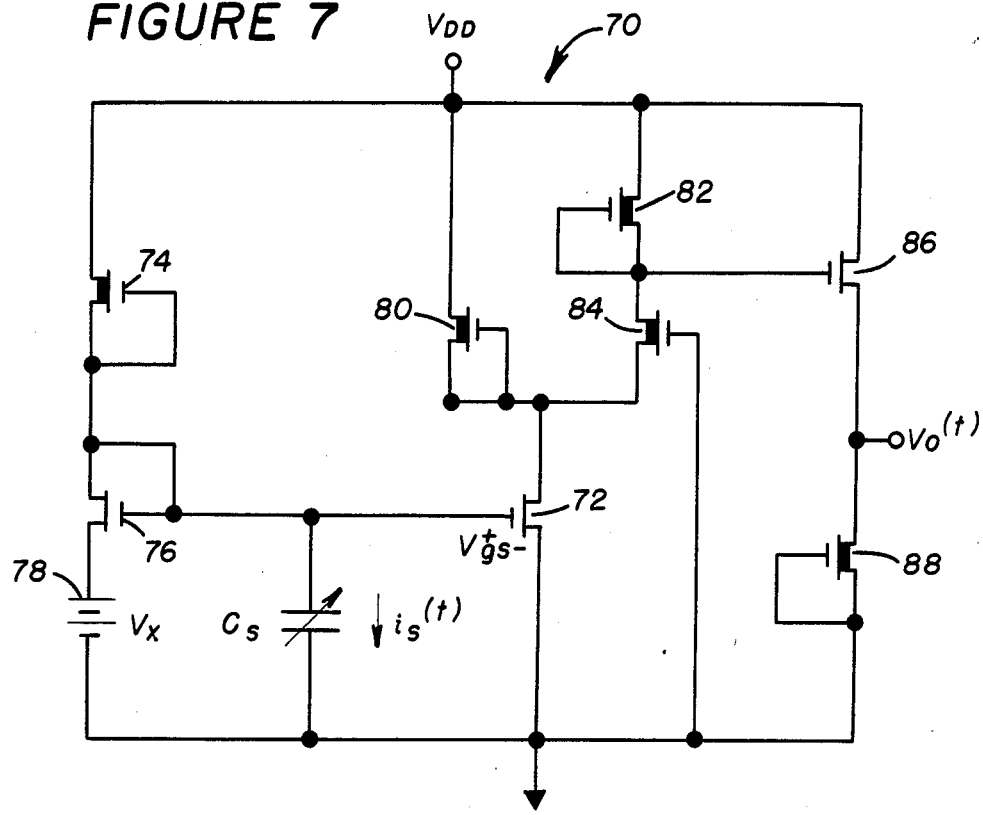
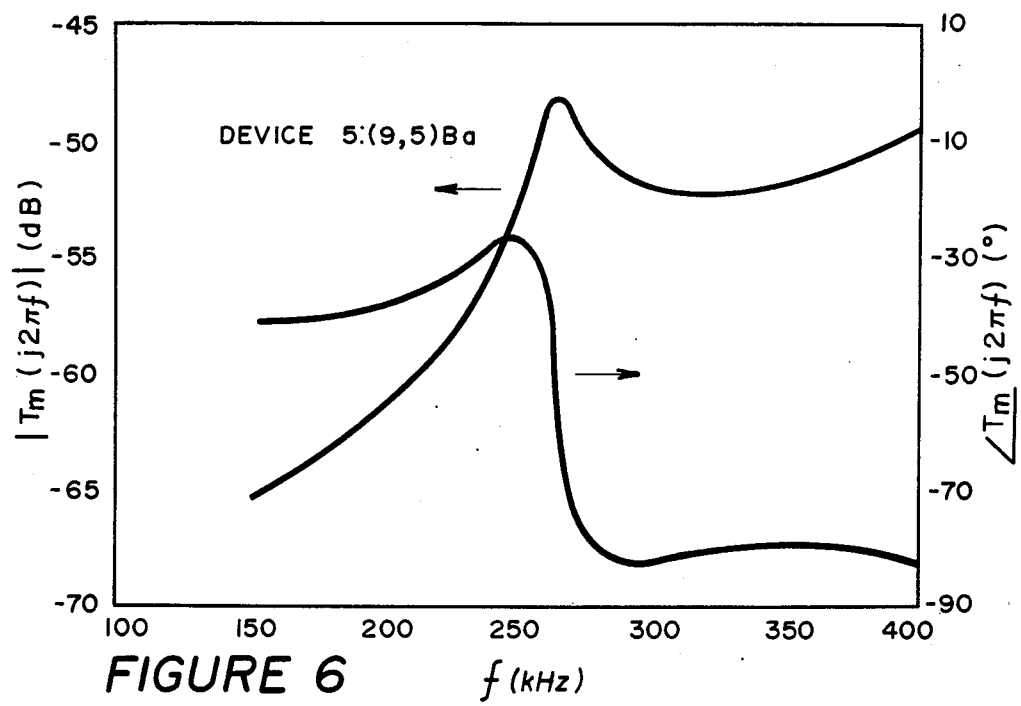
FIGURE 6

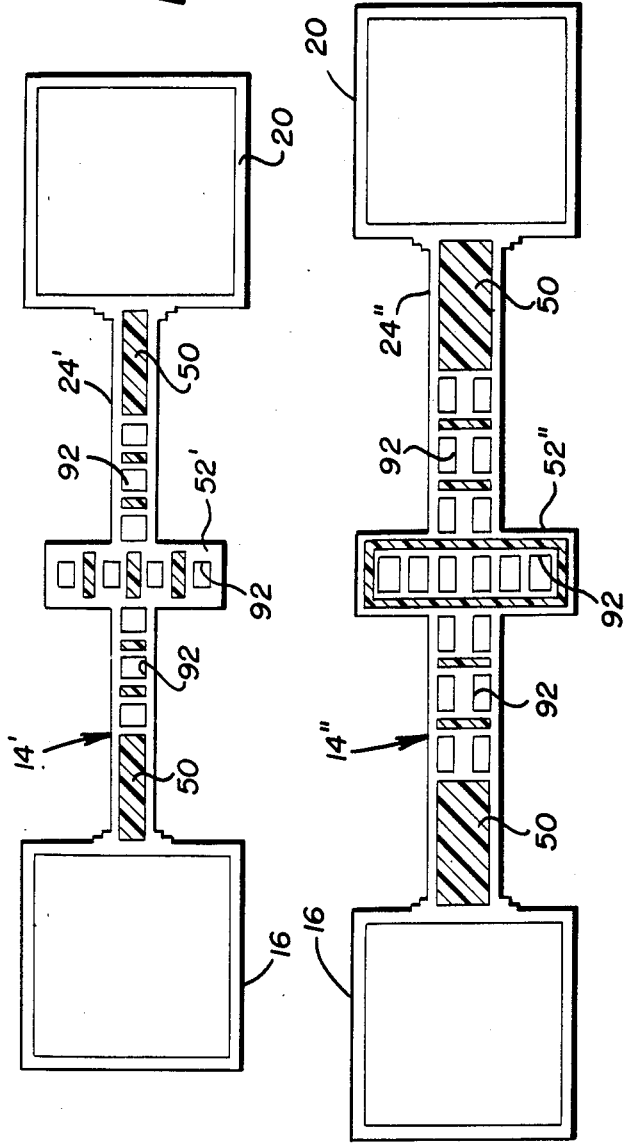
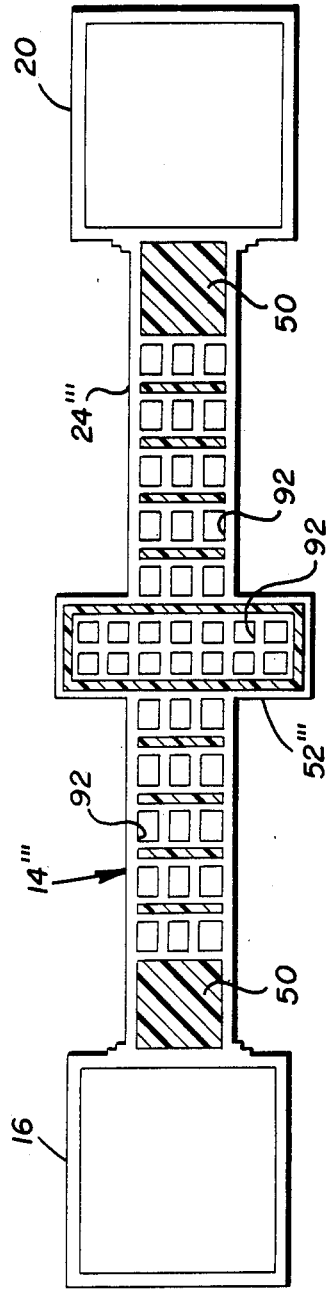

INTEGRATED CIRCUIT SENSOR

This invention is made with Government support under Grants No. ECS-81-20562 and ENG-78-22193 awarded by the National Science Foundation. The Government has certain rights in this invention.

The present invention relates generally to integrated circuit sensors and more particularly to a novel apparatus and a method for constructing such apparatus wherein the integrated circuit sensor includes micro semiconductor structures formed on a semiconductor substrate.

BACKGROUND OF THE INVENTION

Recently, there has been much development in the field of integrated circuit sensors utilizing silicon microstructures. In the prior art, silicon microstructures are made by etching a silicon substrate. Various homogenous and multiple layer cantilever beams and bridges have been made by selectively etching portions of the crystalline silicon that are not protected by an etch resistant layer. A major disadvantage and limitation of etching the silicon substrate is that such etching is not part of conventional integrated circuit planar fabrication technology. The etching step requires special handling during the fabrication of integrated circuits, such is generating a mask layer which may be difficult to control in alignment and tolerances with the standard planar fabrication masks. Furthermore, an anisotropic etchant for silicon, such as a mixture of ethylene diamine, pyrocatechol and water (EDP) or potassium hydroxide (KOH) is utilized to etch the silicon. Neither of the etchants are easily incorporated with conventional IC masking materials.

A known type of integrated circuit sensor useful for detecting the presence of a vapor utilizes a piezoelectric surface acoustic wave (SAW) device. In such a device, a mechanical wave is induced across the surface of the SAW device. A polymer film is disposed along the path of the wave. The polymer film is selected to sorb a gas of interest. In the presence of the gas, the sorption of the gas increases the mass of the polymer film. As the wave intercepts this film, its frequency, phase and time delay across the path of the film change. By detecting these changes, the presence of the vapor of interest is determined. A significant disadvantage and limitation of SAW devices is that they operate at very high frequencies, usually in excess of 10 MHz. At these frequencies, the design of the associated integrated circuit signal processing circuitry becomes more complicated, and hence, less economically feasible. A further disadvantage and limitation of SAW devices is that extra processing and fabrication steps are needed to integrate the piezoelectric with a silicon substrate in which the processing circuitry is fabricated.

SUMMARY OF THE INVENTION

Recently, it has been demonstrated that amorphous or polysilicon layers deposited on an oxide can be formed by etching portions of the polysilicon layer and portions of the oxide beneath the layer to fabricate micro structures such as bridges and cantilever beams. Such polysilicon microstructures have demonstrated excellent mechanical properties with regard to bending, spring tension and tensile forces, for example.

It is therefore an object of the present invention to overcome the disadvantages and limitations of the prior art integrated circuit sensors enumerated above.

An important object of the present invention is to provide an integrated circuit sensor which eliminates etching of the silicon substrate.

Yet another object of the present invention is to provide a novel silicon sensor that utilizes silicon microstructures fabricated on the surface of the substrate.

A further object of the present invention is to fabricate the sensing element compatibly with known integrated circuit fabrication techniques.

Very generally, the integrated circuit sensor of the invention comprises a semiconductor substrate having a first substrate region therein of a conductivity type opposite that of said substrate. A semiconductor layer is provided above the substrate having an overhanging beam portion thereof spaced from the first substrate region and capacitively coupled thereto to form a variable capacitor therewith. A drive circuit is in series with the variable capacitor for applying a drive signal thereto at a preselected frequency to produce vibration in the overhanging beam. A phenomenon sensing medium or device is coupled to the overhanging beam. The phenomenon sensing medium or device in response to a sensed phenomenon changes a selected one of the frequency and the phase of vibration of the overhanging beam. The difference in the selected one of frequency and phase between the drive signal and the vibration of the overhanging beam is detected.

In the preferred embodiment of the invention described herein, an integrated circuit vapor sensor includes a semiconductor substrate and an polycrystalline silicon microstructure disposed on the substrate. The microstructure is shaped to vibrate mechanically. Such shapes may either be in the form of a cantilever beam, a doubly supported beam, or other mechanically vibrating structures such as shells or plates. Several regions of opposite conductivity type to the substrate are disposed beneath the mechanically vibrating structure, such that the mechanically vibrating structure is capacitively coupled to these regions. One such capacitance functions as an excitation capacitor for inducing mechanical vibrations in the vibrating polysilicon microstructure. The excitation capacitor is driven with an AC drive voltage. The frequency of the AC drive voltage is selected commensurately with the resonant frequency of the polysilicon microstructure. As the electrostatic force between the polysilicon microstructure and the substrate changes, a mechanical vibration of the polysilicon microstructure is induced at the frequency of the AC drive voltage.

Another such capacitance functions as the sense capacitor. By applying a constant voltage to the detecting capacitor, the mechanical vibration causes the charge across the capacitor to be modulated at the frequency of the mechanical vibration. The charge modulation can be measured by a change of current through the capacitor. The frequency of such current is also commensurate with the frequency of the mechanical vibration. The presence of the vapor of interest can be detected by providing a polymer thin film on the vibrating microstructure, such film being selected to sorb the vapor of interest. As the mass of the polymer thin film increases, due to the sorption of the vapor, the total mass of the polymer film and the vibrating microstructure increases, causing the resonant frequency of the mechanical vibration to be shifted. By detecting the commensurate one of frequency shift or phase shift of the current through the detecting capacitor, the presence of the vapor is ascertained.

These and other objects, advantages and features of the present invention will become apparent from the following specification when read in conjunction with the accompanying drawings and the appended claims.

BRIEF DESCRIPTION OF THE DRAWINGS

FIG. 6 is a diagrammatic representation of the transfer function of the sensor;

FIG. 7 schematically illustrates a detection circuit, integrated with the sensor of FIG. 1, which is useful for detecting the frequency shift of the mechanical vibrations of the sensor in the presence of a vapor of interest;

FIG. 8A-C represents several embodiments of a microstructure bridge useful in practicing the present invention.

DESCRIPTION OF THE PREFERRED EMBODIMENT

Figures 1, 9:
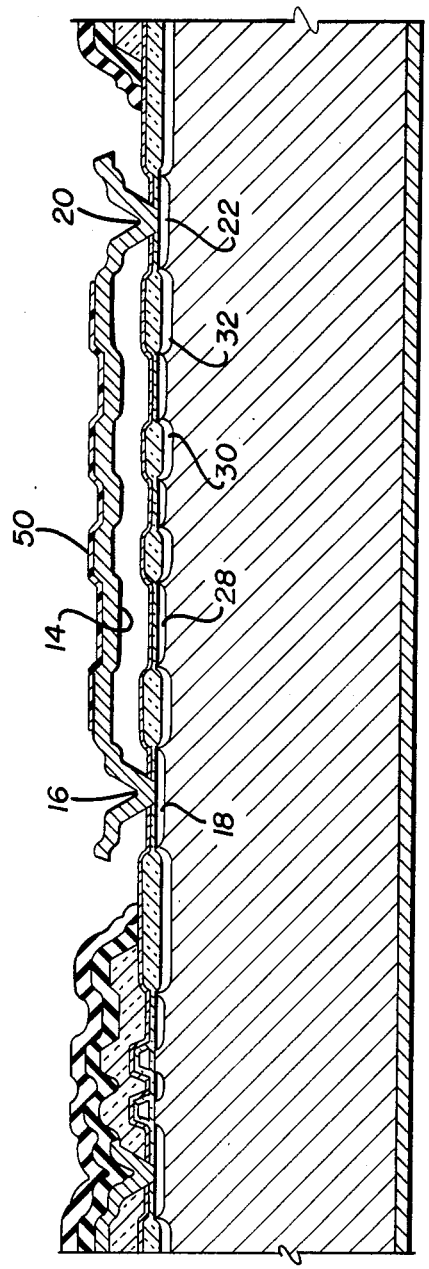
FIG. 1 is a cross-sectional view of an integrated circuit sensor constructed according to the principles of the present invention.
FIG. 9 is a chart illustrating the parameters and performances of the bridge structures of FIG. 8A-C when used in the device of FIG. 1.
Figure 3:
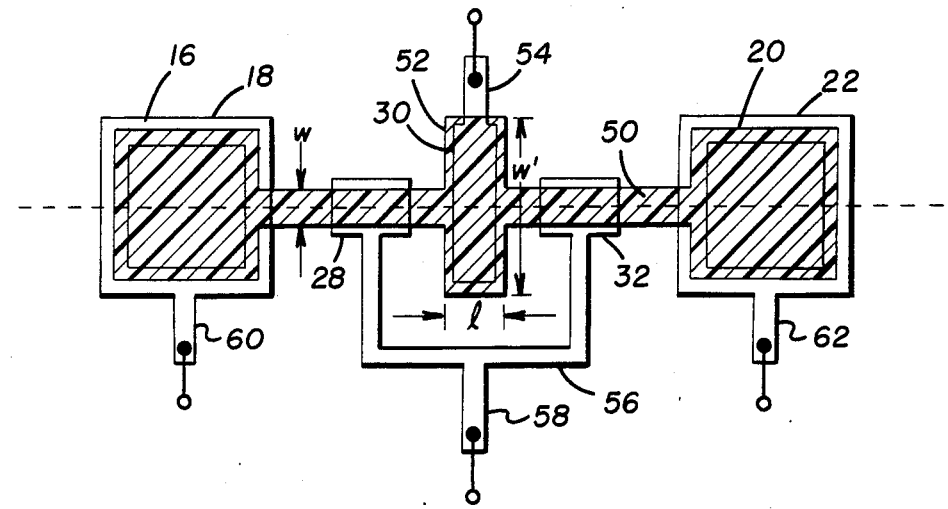
FIG. 3 schematically represents a top view of the sensor shown in FIG. 2.
Figure 2:
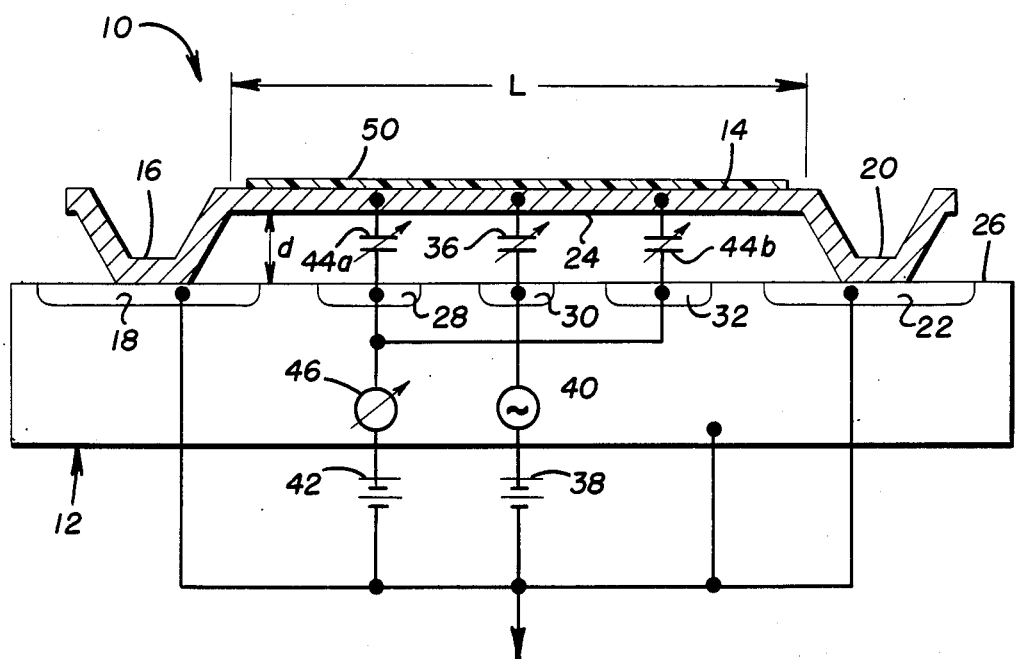
FIG. 2 is a diagrammatic representation of the sensor shown in FIG. 1 useful for explaining the operation of such sensor.

Referring now to FIGS. 1-3, there is shown a silicon integrated circuit sensor 10 constructed according to the principles of the present invention. Sensor 10 includes a substrate 12 of a first conductivity type and a polysilicon microstructure 14 disposed above the substrate. Although the polysilicon microstructure 14 is shown in the shape of a doubly supported beam, it is within the principles of the present invention to provide a cantilever beam structure, or any other polysilicon microstructure which exhibits mechanical vibration, such as plates and shells. As hereinbelow described, the mechanical vibration is used in practicing the present invention.

Polysilicon microstructure 14 has an end portion 16 being electrically coupled to a substate region 18 of a second conductivity type opposite the first conductivity type. The other end portion 20 of polysilicon microstructure 14 is also electrically coupled to a further substrate region 22 of the second conductivity type. An intermediate portion between end portions 16 and 20 of polysilicon microstructure 14 forms a doubly supported beam or bridge 24 which is spaced from a surface 26 of substrate 12 by a selected distance D. Bridge 24 is further capacitively coupled to each of substrate regions 28, 30 and 32, these substrate regions 28, 30 and 32 also being of the second conductivity type. For purposes of the following description, the capacitance between bridge 24 and each of substrate regions 28 and 32 form half of a detection capacitor, $C_S$. The capacitance between bridge 24 and substrate region 30 forms the excitation capacitor 36.

Substrate region 18 and substrate region 22 are electrically coupled together and biased at a reference potential, such as ground as best seen in FIG. 2. The reference potential is also coupled to silicon microstructure 14 through electrical coupling between microstructure end portions 16 and 20 to substrate regions 18 and 22, respectively. An initial charge is obtained on the excitation capacitor 36 by coupling a DC voltage source 38 between the reference potential and substrate region 30. Superimposed upon the DC source 38, by being electrically coupled in series therewith, is an alternating voltage source 40 coupled between substrate region 30 and DC source 38. DC source 38 provides an initial charge on capacitor 36, wherein the charge repulsion results in a deflection of bridge 24 away from the surface 26 of substrate 12. As the voltage across capacitor 36 is modulated by the alternating voltage of source 40, the charge across capacitor 36 is modulated at the same frequency as the voltage provided by source 40. Thus, as the mechanical repulsion of the charge of capacitor 36 is modulated, beam 24 will oscillate at the same frequency as the frequency provided by voltage source 40. The frequency of voltage source 40 is selected, in one embodiment of the present invention, to be commensurate with the first order vibrational harmonic frequency of beam 24.

A second DC voltage source 42 is coupled between the source of reference potential and each of substrate regions 28 and 32 to obtain an initial charge on sense capacitors 44a and 44b, each forming one-half of the sense capacitor, $C_S$, by being coupled in parallel. As the vibration of beam 24 changes the separation between the plates of capacitors 44a and 44b, the charge provided by voltage source 42 is modulated at the frequency of the mechanical vibration. This charge modulation in the sense capacitors 44a and 44b will then induce a current through these capacitors 44a and 44b which may be detected, as schematically shown by ammeter 46. The frequency of this current will be commensurate with the frequency of vibration of bridge 24. The complete detection circuit is fully described herein below with reference to FIG. 7.

A polymer film 50 is disposed on the surface of bridge 24. Polymer film 50 is selected to sorb the vapor of interest. As the vapor is sorbed, the mass of film 50 will change, thereby modulating the resonant frequency of bridge 24, which is determined by the total mass of bridge 24 and film 50. This change of the resonant frequency to a second frequency is detected by capacitors 44a and 44b. Furthermore, the current developed through the sense capacitors 44a and 44b will have a frequency commensurate with the mechanical vibration frequency of bridge 24. Detecting the frequency shift of this current will transduce the detection of the vapor of interest.

Figure 4:
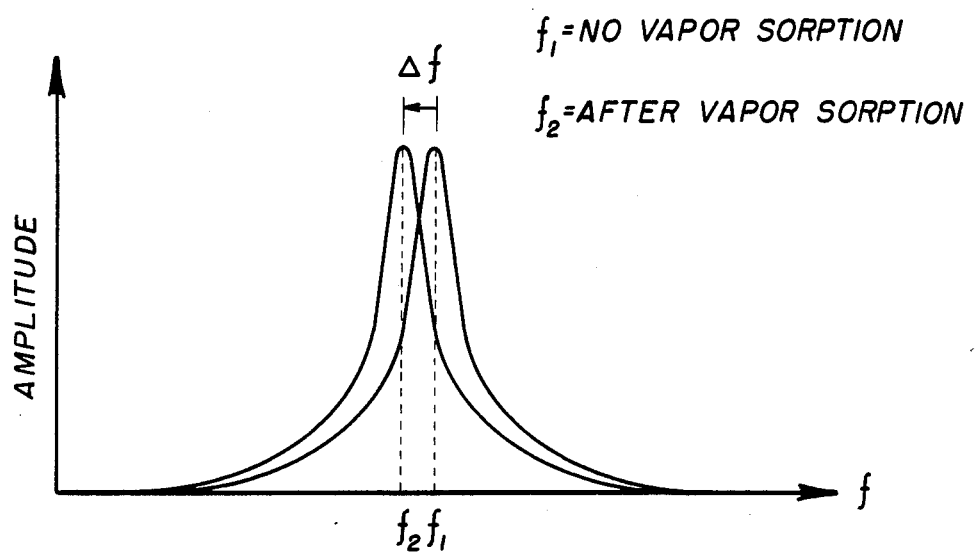
FIGS. 4 and 5 diagrammatically represent a qualitative frequency and phase shift of the detecting capacitor current occurring as a result of vapor sorption by the polymer thin film.
Figure 5:
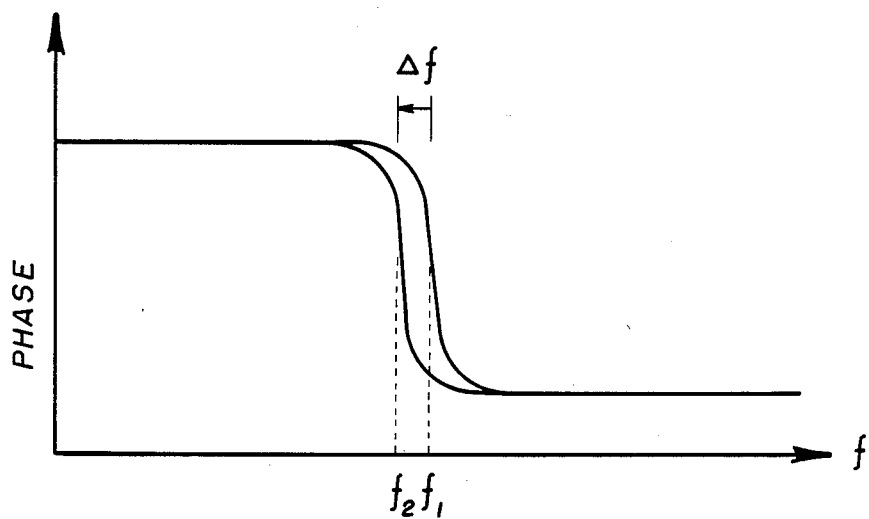

Referring also to FIG. 4, the qualitative frequency shift from the resonant frequency, $f_1$, to the second frequency, $f_2$, in the presence of the vapor of interest is shown. FIG. 5 illustrates the phase of the frequency shift as it crosses resonance at either the first frequency, $f_1$, or the second frequency, $f_2$.

As best seen in FIG. 3, bridge 24 of microstructure 14 includes a laterally elongated portion 52 disposed over substrate region 30. Elongated portion 52 provides for increased electrostatic coupling between bridge 24 and substrate region 30. Extending from substrate region 30 is a channel 54, of the same conductivity type of region 30, to which alternating voltage source 40 is coupled. A channel 56 is illustrated coupling substrate regions 28 and 32. An extension 58 of channel 56 provides coupling to DC bias source 42 and the detection circuit 46, each of which are more fully described hereinbelow with reference to FIG. 7. For purposes of structural integrity, end portions 16 and 20 of microstructure 14 are enlarged pads to provide sufficient contact area to the associated substrate region 18 and 22. Thus, bridge 24 is a narrowed portion of microstructure 14 extending between end portions 16 and 20. Elongated channels 60 and 62 extend from the respective substrate regions 18 and 22. These channels 60 and 62 are useful for coupling substrate regions 18 and 22 to the reference potential.

Referring now also to FIG. 6, there is shown the overall measured electromechanical transfer functions of sensor 10. Note that the absolute value of the gain of transfer functions shows a sharp increase towards a resonant frequency, followed by a declining gain portion and then followed by another rising gain portion. As qualitatively shown in FIG. 5, a phase shift occurs at the point of resonant frequency but otherwise remains relatively constant on either side of the resonant frequency. Thus FIG. 6 illustrates that to sense the vapor of interest, either the frequency or phase shift the vibrating polysilicon microstructure may be detected. In some embodiments of the present invention, the phase shift occurring in the presence of the vapor of interest may be more pronounced than the frequency shift, as qualitatively shown in FIG. 6.

Referring now to FIG. 7, there is shown a detailed representation of a detecting circuit 70 which was schematically illustrated as voltage source 42 and ammeter 46 in FIG. 2. Detecting circuit 70 includes a drive transistor 72, whose gate-source voltage, $V_{gs}$, provides the DC voltage of source 42 (FIG. 2). The gate-source voltage, $V_{gs}$, of drive transistor 72 is determined from a constant current depletion source transistor 74 having its gate electrically coupled to its source and a diode connected enhancement mode transistor 76 with its source electrically coupled to its gate. Coupled between the reference ground potential and the drain of transistor 76 is an externally applied voltage source 78 at a voltage $V_x$. The drain of transistor 74 is connected to the external DC voltage $V_{DD}$. The series connection of transistor 74, transistor 76 and voltage source 78 ensure that a constant DC voltage occurs at the source of transistor 76 which is electrically coupled to the gate of drive transistor 72. Voltage source 78 is required to compensate for mismatches in the depletion and enhancement threshold voltages of transistor 74 and transistor 76, respectively. Source 78 could be eliminated if these depletion and enhancement threshold voltages are tightly controlled. A capacitor 80, having a capacitance $C_s$, is illustrated coupled between the gate of drive transistor 72 and reference potential. This capacitance $C_s$ is equivalent to the parallel coupled capacitors 44a and 44b as described hereinabove in FIG. 2. The charge modulation across the capacitance $C_s$ is illustrated by the current $I_s(t)$. The modulation of the capacitance $C_s$ provides a small signal modulation of the gate-source voltage, $V_{gs}$, of drive transistor 72. To increase the drain current of drive transistor 72, a depletion mode current source transistor 80 is coupled between the drain of transistor 72 and the externally applied DC voltage $V_{DD}$. Furthermore, the drain of drive transistor 72 is coupled to a high-impedance, depletion-load inverter transistor 82 whose drain is coupled to the external DC bias voltage $V_{DD}$. To increase the gain of depletion load inverter 82, the drain and source of a buffer transistor 84 is coupled to the source of depletion load inverter transistor 82 and the drain of drive transistor 72, respectively. The gate of depletion mode buffer transistor 84 is coupled to the ground reference potential. The source of depletion load inverter transistor 82 is coupled to the gate of a transistor 86 whose drain is coupled to the externally applied DC bias voltage $V_{DD}$ and whose source is coupled to an output voltage $V_o(t)$ which transduces the current $I_s(t)$ through capacitance $C_s$ into a voltage $V_o(t)$. Coupled between the output voltage $V_o(t)$ and the reference potential is depletion mode current source transistor 88. Transistor 86 and 88 provide a source follower buffer for the output signal developed by depletion load inverter 82. The output voltage $V_o$, taken at the node between transistor 86 and transistor 88 is a function of the sense current $I_s$ times the derivative of the sense capacitance $C_s$ (capacitors 44a and 44b of FIG. 2).

Referring now to FIGS. 8A–C there are shown several embodiments of microstructure 14. In FIG. 9, the dimensions for each structure in FIGS. 8A, 8B and 8C are shown along with its measured resonant frequency and its quality factor. For example, the bridge 24 in FIG. 8A has a length of 122 micrometers, a width of 9 micrometers, a thickness of 14 micrometers and a lateral center portion width of 39 micrometers. For a solid bridge, with similar dimensions to the bridge shown in FIG. 8A and without the holes therein, its resonant frequency is shown to be 433.5 kHz. However, by the addition of holes 92 as shown therein, the resonant frequency is reduced to 449 kHz. Similarly, FIG. 9 shows the representative dimensions for the bridges as shown in FIGS. 8B and 8C along with the resonant frequencies and quality factors with the absence or presence of holes. The holes 92 communicate between a first surface and a second surface in a facing relationship with the first surface of the semiconductor layers 14', 14'', 14'''. Furthermore, the holes 92 are disposed in the direction of the mechanical vibration. Therefore, the bridges having holes 92 have higher, or enhanced, quality factors due to reduced air damping, as demonstrated by the data in FIG. 9. The use of holes 92 allows the quality factor to be tailored to give a desired overall transfer function. The bridges shown in FIGS. 8A–C can be included in a single sensor to form an array of bridges. Each of the bridges would be electrically connected to the same connectors but operating at different resonant frequencies. The different frequency drive and sense signals for each of the bridges would then be multiplexed.

There has been described a novel integrated circuit sensors and techniques. It is now obvious that those skilled in the art may make numerous uses of and modifications to the present invention without departing from the inventive concepts disclosed herein. Accordingly, the invention is to be defined solely by and limited only by the following claims.

What is claimed is:

1. An integrated circuit sensor comprising:
   a substrate of a first conductivity type having first and second substrate regions of a second conductivity type opposite said first conductivity type;
   a semiconductor layer having a first portion and a second portion, said second portion being spaced from said substrate and capacitively coupled to said first and second substrate regions, said first portion being motionally fixed with respect to said substrate;

drive means for inducing a mechanical vibration in said second portion of said semiconductor layer by applying an electrical signal at a selected one of a first frequency and a first phase across said second portion and said second substrate region to vary the capacitance between said second portion of said semiconductor layer and said first substrate region at said first frequency and phase;

means coupled to said semiconductor layer for shifting a selected one of the frequency and the phase of said mechanical vibration to one of a second frequency and a second phase in response to a sensed phenomenon; and detecting means coupled across said second portion of said semiconductor layer and said first substrate region and being responsive to the varying capacitance between said second portion and said first substrate region for detecting the selected one of a frequency shift and a phase shift between said first frequency and said second frequency and said first phase and said second phase, respectively.

2. A sensor as set forth in claim 1 wherein said shifting means includes:
a polymer film disposed on said second portion of said semiconductor layer, said polymer film being selected to sorb the vapor of interest.

3. A sensor as set forth in claim 1 wherein said mechanical vibration inducing means includes:
a second substrate region of said second conductivity type, said first portion of said semiconductor layer being electrically coupled to said second substrate region;
a third substrate region of said second conductivity type capacitively coupled to said second portion of said semiconductor layer; and
means for applying a voltage at said selected first frequency between said second substrate region and said third substrate region.

4. A sensor as set forth in claim 1 wherein said detecting means includes:
means for applying a constant voltage between said first substrate region and said second portion of said semiconductor layer;
means for developing a current in response to the varying capacitance between said first substrate region and said second portion of said semiconductor layer, said current having a frequency and a phase commensurate with the frequency and phase of said mechanical vibration; and
means for detecting the selected one of said frequency shift and said phase shift of said current.

5. A sensor as set forth in claim 1 wherein said semiconductor layer is fabricated from polysilicon.

6. An integrated circuit sensor comprising:
a substrate of a first conductivity type having first and second substrate regions of a second conductivity type opposite said first conductivity type;
a semiconductor layer having a first portion, a second portion and a third portion intermediate said first portion and said second portion, said third portion forming a bridge spaced from said substrate and capacitively coupled to said first and second substrate regions, each of said first portion and said second portion being motionally fixed with respect to said substrate;

drive means for inducing a mechanical vibration in said bridge by applying an electrical signal at a selected one of a first frequency and a first phase across said bridge and said second substrate region to vary the capacitance between said bridge and said first substrate region at said selected frequency and phase;

means coupled to said bridge for shifting a selected one of the frequency and the phase of said mechanical vibration to one of a second frequency and a second phase in response to a sensed phenomenon; and detecting means coupled across said bridge and said first substrate region and being responsive to the varying capacitance between said bridge and said first substrate region for detecting the selected one of a frequency shift and a phase shift between said first frequency and said second frequency and said first phase and said second phase, respectively.

7. A sensor as set forth in claim 6 wherein said shifting means includes a polymer film disposed on said bridge selected to sorb the vapor of interest.

8. A sensor as set forth in claim 6 wherein said inducing means includes:
a second substrate region of said second conductivity type, one of said first portion and said second portion of said semiconductor layer being in electrically coupled to said second substrate region;
a third substrate region of said conductivity type capacitively coupled to said bridge; and
means for applying a voltage at said selected first frequency between said second substrate region and said third substrate region.

9. A sensor as set forth in claim 8 wherein said inducing means further includes:
a fourth substrate region of said conductivity type, the other of said first portion and said second portion of said semiconductor layer being electrically coupled to said fourth substrate region, said fourth substrate region being electrically coupled to said second substrate region.

10. A sensor as set forth in claim 9 wherein said inducing means further includes:
a fifth substrate region of said second conductivity type electrically coupled to said third substrate region, and capacitively coupled to said bridge, said third substrate region being disposed intermediate said first substrate region and said second substrate region, said fifth substrate region being disposed intermediate said first substrate region and said fourth substrate region.

11. A sensor as set forth in claim 10 wherein said inducing means further includes means for applying a constant voltage between said first substrate region and each said second substrate region and fourth substrate region to provide an initial charge across the capacitance between said bridge and said first substrate region.

12. A sensor as set forth in claim 6 wherein said semiconductor layer is fabricated from polysilicon.

13. A sensor as set forth in claim 6 wherein said semiconductor layer has a first surface, a second surface in a facing relationship with said first surface and a plurality of openings communicating between said first surface and said second surface.

14. A sensor as set forth in claim 13 wherein said openings are disposed in the direction of the mechanical vibration of said semiconductor layer.

15. An integrated circuit sensor comprising:
- a semiconductor substrate having a first substrate region therein of a conductivity type opposite that of said substrate;
- a semiconductor layer on said substrate having a cantilever portion thereof spaced from said first substrate region and capacitively coupled thereto to form a variable capacitor therewith;
- a drive circuit in series with said variable capacitor for applying a drive signal thereto at a preselected frequency to produce vibration in said cantilever portion of said semiconductor layer;
- means coupled to said cantilever portion of said semiconductor layer responsive to a sensed phenomenon for changing the frequency of vibration of said cantilever portion in response to a sensed phenomenon; and
- means for detecting the difference in frequency between the drive signal and the vibration of said cantilever portion, said detecting means including a capacitive means on said cantilever portion and said substrate for developing an electrical signal having a frequency commensurate with the frequency of the vibration of said cantilever portion; and
- means for detecting the difference between said drive signal and said electrical signal.

16. The sensor as set forth in claim 15 wherein said developing means includes a second substrate region of a conductivity type opposite that of said substrate, said cantilever portion spaced from said second substrate region and capacitively coupled thereto to form a sense variable capacitor therewith;
- means for applying a constant voltage to said sense capacitor;
- means for detecting current developed through said sense capacitor as a result of variation of said sense capacitor due to the vibration of said cantilever portion, the frequency of said current being commensurate with such vibration; and
- means for detecting frequency shift of said current from the frequency of said drive signal.

* * * * *